US009932203B2

United States Patent
Robibero (10) Patent No.: US 9,932,203 B2
(45) Date of Patent: Apr. 3, 2018

(54) METHOD AND DEVICE FOR DETECTING A DETERIORATION STATE OF A LOAD BEARING CAPACITY IN A SUSPENSION MEMBER ARRANGEMENT FOR AN ELEVATOR

(71) Applicant: Inventio AG, Hergiswil (CH)

(72) Inventor: Vincent Robibero, Randolph, NJ (US)

(73) Assignee: INVENTIO AG, Hergiswil (CH)

( * ) Notice: Subject to any disclaimer, the term of this patent is extended or adjusted under 35 U.S.C. 154(b) by 426 days.

(21) Appl. No.: 14/814,558

(22) Filed: Jul. 31, 2015

(65) Prior Publication Data
US 2017/0029249 A1    Feb. 2, 2017

Related U.S. Application Data
(60) Provisional application No. 62/199,375, filed on Jul. 31, 2015.

(51) Int. Cl.
  *B66B 1/34*  (2006.01)
  *B66B 7/12*  (2006.01)
  *G01R 31/08* (2006.01)

(52) U.S. Cl.
  CPC .......... *B66B 7/1223* (2013.01); *B66B 7/1215* (2013.01); *G01R 31/08* (2013.01)

(58) Field of Classification Search
  CPC ...... B66B 7/1223; B66B 7/1215; G01R 31/08
  (Continued)

(56) References Cited

U.S. PATENT DOCUMENTS 5,731,528 A * 3/1998 Yamazaki ............... G01L 5/042
                                                          73/828
6,040,779 A * 3/2000 Pfaff ........................ G01D 3/08
                                                          324/706
(Continued)

FOREIGN PATENT DOCUMENTS

DE    19708518 A1   10/1998
EP    1730066 B1    10/2010
(Continued)

OTHER PUBLICATIONS

Huaming Lei et al., "Health Monitoring for Coated Steel Belts in an Elevator System" Journal of Sensors, vol. 2012, pp. 1-5. Article ID 750261.

*Primary Examiner* — Anthony Salata
(74) *Attorney, Agent, or Firm* — Williams J. Clemens; Shumaker, Loop & Kendrick, LLP (57) ABSTRACT

A deterioration state of load bearing capacity in an elevator suspension member having a plurality of electrically conductive cords is detected by: providing a multi-phase alternating current circuitry including electrically conductive legs; applying at least one phase of a multi-phase alternating current to at least one of the cords electrically connected to one of the legs; applying at least another phase of the current to at least another cord and at least one resistor electrically connected to at least another leg; measuring an electric indicator current being at least one of a net sum of all phases of the current and an electric bypass current through a neutral wire being connected in parallel to the circuitry, wherein a peak current in each phase is shifted by a phase angle with respect to a peak current in another phase; and determining the deterioration state based on the measured indicator electric current.

18 Claims, 6 Drawing Sheets

(58) Field of Classification Search
USPC ....... 187/247, 391, 393; 324/71.1, 539, 691, 324/693, 695, 700, 705, 706, 718, 725
See application file for complete search history.

(56) References Cited

U.S. PATENT DOCUMENTS

| | | | |
|---|---|---|---|
| 6,422,088 B1* | 7/2002 | Oba | G01D 3/08 |
| | | | 73/754 |
| 6,653,943 B2* | 11/2003 | Lamb | B66B 7/1223 |
| | | | 324/513 |
| 6,828,771 B1 | 12/2004 | Ghassemi | |
| 7,123,030 B2 | 10/2006 | Robar et al. | |
| 8,011,479 B2 | 9/2011 | Stucky et al. | |
| 8,424,653 B2 | 4/2013 | Stucky et al. | |
| 8,686,747 B2* | 4/2014 | Berner | B66B 7/1223 |
| | | | 187/391 |
| 8,813,918 B2* | 8/2014 | Kocher | B66B 7/1223 |
| | | | 187/391 |
| 9,599,582 B2* | 3/2017 | Fargo | G01N 27/20 |
| 2002/0194935 A1* | 12/2002 | Clarke | B66B 7/1223 |
| | | | 73/862.391 |
| 2003/0121729 A1* | 7/2003 | Heinz | B66B 7/062 |
| | | | 187/254 |
| 2008/0223668 A1 | 9/2008 | Stucky et al. | |
| 2008/0282512 A1 | 11/2008 | Ach | |
| 2011/0284331 A1 | 11/2011 | Stucky et al. | |
| 2013/0207668 A1 | 8/2013 | Fargo et al. | |
| 2016/0002006 A1* | 1/2016 | Sun | B66B 7/1223 |
| | | | 187/254 |

FOREIGN PATENT DOCUMENTS

| | | |
|---|---|---|
| EP | 1732837 B1 | 4/2011 |
| WO | 2005095250 A1 | 10/2005 |
| WO | 2010007112 A1 | 1/2010 |
| WO | 2011098847 A1 | 8/2011 |
| WO | 2013135285 A1 | 9/2013 |
| WO | 2014083043 A1 | 6/2014 |
| WO | 2014130028 A1 | 8/2014 |
| WO | 2014130029 A1 | 8/2014 |

* cited by examiner

METHOD AND DEVICE FOR DETECTING A DETERIORATION STATE OF A LOAD BEARING CAPACITY IN A SUSPENSION MEMBER ARRANGEMENT FOR AN ELEVATOR

FIELD

The present invention relates to a method and to a device for detecting a deterioration state of a load bearing capacity in a suspension member arrangement for an elevator.

BACKGROUND

Elevators typically comprise a car and, optionally, a counterweight which may be displaced for example within an elevator shaft to different levels in order to transport persons or items for example to various floors within a building. In a common type of elevator, the car and/or the counterweight are supported by a suspension member arrangement comprising one or more suspension members. A suspension member may be a member which may carry heavy loads in a tension direction and which may be bent in a direction transverse to the tension direction. For example, a suspension member may be a rope or a belt. Typically, suspension members comprise a plurality of cords. The cords may be made for example with a metal such as steel.

During operation of the elevator, suspension members have to carry high loads and are typically repeatedly bent when running along for example a traction sheave, a deflection sheave or other types of sheaves. Accordingly, substantial stress is applied to the suspension member arrangement during operation.

However, as elevators may typically be used by people for transportation along very significant heights, very high security requirements have to be fulfilled. For example, it has to be safeguarded that the suspension member arrangement can always guarantee safe support of the car and/or the counterweight. For such purposes, safety regulations rule that any substantial deterioration of an initial load bearing capacity of a suspension member arrangement can be detected such that for example counter-measures such as replacing a faulty suspension member from the suspension member arrangement may be initiated.

Generally, a load bearing capacity of a suspension member may be specified when designing the suspension member and may then be physically tested upon completion of the fabrication of the suspension member. Physical tests may comprise for example tensile loading of the suspension member and measuring the suspension member's reaction to an application of high tensile forces.

However, during actual operation of the elevator, it may be difficult or even impossible to perform such physical tests. With conventional steel ropes serving as suspension members, visual checking of a rope condition has been possible. However, in modern suspension members, load bearing cords are typically enclosed in a coating or matrix and are therefore not visible from outside. Therefore, alternative approaches for determining a load bearing capacity in a suspension member arrangement or determining parameters related thereto have been developed.

For example, elevator load bearing member wear and failure detection has been described in EP 1 730 066 B1. A method and apparatus for detecting elevator rope degradation using electrical resistance is described in U.S. Pat. No. 7,123,030 B2. Electrical signal application strategies for monitoring a condition of an elevator load bearing member are described in US 2011/0284331 A1 and U.S. Pat. No. 8,424,653 B2. Electrical signal application strategies for monitoring a condition of an elevator load bearing member are described in US 2008/0223668 A1 and U.S. Pat. No. 8,011,479 B2. A simplified resistance based belt type suspension inspection is disclosed in US 2013/0207668 A1. An elevator system belt type suspension having connecting devices attached thereto is described in WO 2011/098847 A1. A method for detection of wear or failure in a load bearing member of an elevator is described in WO 2013/135285 A1. Electrical signal application strategies for monitoring a condition of an elevator load bearing member are described in EP 1 732 837 B1. "Health Monitoring for Coated Steel Belts in an Elevator System" have been described in a research article of Huaming Lei et al. in the Journal of Sensors, Volume 2012, Article ID 750261, 5 pages, doi: 10.1155/2012/750261.

There may be a need for an alternative method and device for detecting a deterioration state of a load bearing capacity in a suspension member arrangement for an elevator. Particularly, there may be a need for such method and device which enable fulfilling high safety requirements, simple implementation and/or low cost.

SUMMARY

A first aspect of the present invention relates to a method for detecting a deterioration state of a load bearing capacity in a suspension member arrangement for an elevator, the suspension member arrangement comprising at least one suspension member having a plurality of electrically conductive cords. These cords may be electrically isolated from each other. The method comprises the following steps: a multi-phase alternating current circuitry including multiple electrically conductive legs is provided. At least one phase of a multi-phase alternating current is applied to at least one of the cords of the suspension member by being electrically connected to one of the legs of the multi-phase alternating current circuitry. At least one other phase of the multi-phase alternating current is applied to another at least one cord of the suspension member and/or to at least one separate resistor, wherein the cord and/or the resistor is electrically connected to at least one other leg of the multi-phase alternating current circuitry. Therein, in the multi-phase alternating current, a peak current in each phase is shifted by a phase angle with respect to a peak current in another phase, such shifting phase angle being e.g. 180°, 120°, 90° or more generally 360°/n (with n being the number of phases). In such arrangement, an electric current being named herein as "indicator current" and being a net sum of all phases of the multi-phase alternating current and/or an electric bypass current through a neutral wire being connected in parallel to the multi-phase alternating current circuitry, is measured. Based on such measured electric indicator current, the deterioration state is finally determined.

Without restricting the scope of the invention in any way, ideas underlying embodiments of the invention may be understood as being based, inter alia, on the following recognitions and observations:

In conventional approaches for detecting a deterioration state of a load bearing capacity in a suspension member arrangement such as those approaches indicated in the above introductory portion, electrical characteristics of cords included in a suspension member have been taken as indicators for changes in the deterioration state. Generally, electrical resistances within the cords have been measured and it has been assumed that an increase of such electrical resistances indicates a deterioration of the load bearing capacity of the suspension member.

However, such electrical resistance measurements, or alternatively impedance measurements, may require substantial efforts in terms of, e.g., measuring devices, measurement analyzing devices, circuitry, etc. For example, electrical resistances have to be included, measured and compared within circuitry comprising cords of a suspension member in order to thereby enable quantitative measurements of the electrical resistance or impedance of the cords.

The inventors of the present invention have found that measuring electrical resistance/conductivity of cords, particularly measuring quantitatively such characteristics, is not necessary in order to obtain sufficient information about a deterioration state of a load bearing capacity in a suspension member to ensure safe operation of an elevator.

As an alternative approach to conventional methods and devices, it is therefore proposed to not necessarily measure any electrical resistance, resistivity or impedance within conductive cords of a suspension member directly but to provide for a method which allows for deriving sufficient information about a deterioration state by measuring one or more electric currents which at least relate to electric currents flowing through cords of the suspension member.

In such alternative approach, electrical resistances, resistivities or impedances do neither have to be known quantitatively on an absolute scale nor in a relative manner. Instead, it may be sufficient to simply measure an electric current, particularly a time-dependent change in such electric current, without having any detailed knowledge about actual resistances, resistivities and/or impedances through the cords of the suspension member.

The idea underlying the inventive method may be briefly summarized as follows: One or more of the cords of a suspension member may be made part of a multi-phase alternating current circuitry by connecting it preferably in series with at least one of the legs of such multi-phase alternating current circuitry. Accordingly, at least one phase of a multi-phase alternating current is directed through this leg (or these legs) and therefore flows through the respective cord(s). One or more other phases of the same multi-phase alternating current are either directed through other cords of the same or other suspension members of the suspension member arrangement or are directed through one or more separate resistors by connecting these other cords or separate resistors electrically to at least one other leg of the multi-phase alternating current circuitry. Therein, the term "resistor" may be interpreted as representing any type of electrical load including for example load with electrical impedance. In other words, at least one of the phases of the multi-phase alternating current flows through a portion of the suspension member arrangement by being applied to at least one of its cords whereas at least one other phase may also flow through cords of the suspension member arrangement or may be directed through separate resistors. In such multi-phase arrangement, the phases of the multi-phase alternating current flow through the various legs of the multi-phase alternating current circuitry with a specific phase relationship. Generally, physical characteristics of the suspension member directly result in changes in its electrical characteristics, i.e. changes in electro-physical characteristics of e.g. cords in the suspension member may result from e.g. a change in the diameter of the cords, from any shorts or shunts, from breaks, etc. In case physical characteristics of the suspension member and electrical characteristics relating to such physical characteristics change over time, the phase relationship in a multi-phase alternating current will generally change.

The change in such phase relationship may be measured relatively easily. In one approach, such phase relationship change may be determined by measuring an electric indicator current resulting as a net sum of all phases of the multi-phase alternating current. Such net sum directly depends on the phase relationship between the various phases such that changes in the net sum electric current allow deriving information about the electrical characteristics and therefore the deterioration state of the load bearing capacity of the suspension member arrangement. Alternatively to measuring the net sum of all phases of the multi-phase alternating current, an electrical bypass current through a neutral wire being connected in parallel to the multi-phase alternating current circuitry may be measured. Such bypass current through the neutral wire directly depends on the various phase currents flowing through the legs of the multi-phase alternating current circuitry. Therefore, a change in such bypass current may also enable deriving information about the electrical characteristics and therefore the deterioration state of the load bearing capacity in the suspension member arrangement. All these measurements do not require any direct or indirect measuring of resistances within the cords of a suspension member but it may be sufficient to measure an electric indicator current only.

Particularly, according to an embodiment, the deterioration state may be determined based on a deviation of the measured electric indicator current from a reference current value.

For example, an initial value of the measured indicator current may be determined upon installation of the suspension member arrangement in the elevator in a non-deteriorated state and such initial value can be taken as the reference current value. Alternatively, such reference current value may be determined based on other measurements, calculations and/or assumptions. During the operation of the elevator, the same or a corresponding indicator current may be measured with the multi-phase alternating current circuitry described herein. In case such subsequently measured indicator electric current substantially deviates from the reference current value, this may be taken as indicating a substantial deterioration in the load bearing capacity of the suspension member.

Particularly, according to an embodiment, a critical deterioration state may be detected upon the measured electric indicator current deviating from the reference current value by more than a predetermined difference value.

In other words, a specific difference value may be predetermined. For example, physical tests may be made in order to obtain information on how electrical characteristics of cords in a suspension member change upon physical stress and current values may be determined based on such physical tests. From such preceding experiments, the predetermined difference value may be derived such that, in later normal operation of the elevator, the electric indicator current being the indicator for the deterioration state may be repeatedly or continuously measured and a critical deterioration state may be assumed as soon as changes in this measured indicator current exceed the predetermined difference value. Upon detecting such critical deterioration state, counter-measures such as for example replacing the respective suspension member may be initiated.

According to an embodiment, the electric current is measured using a measuring arrangement comprising a measuring device for contactless measuring of an electrical current in a conductor arrangement.

One possible option for contactless measuring of an electrical current is based on induction. Every electrical current in a conductor arrangement creates a magnetic field and changes in the current result in variations in the magnetic field which may then be used for inductively coupling the conductor arrangement in which the electrical current to be measured flows with a conductor arrangement of the measuring device. Contactless measuring of an electrical current enables a very simple measurement. For example, no direct physical connection needs to exist between the measuring device and the conductor arrangement. Instead, the measuring device may be arranged slightly spaced apart from the conductor arrangement in which the electrical current to be measured flows and/or may be electrically isolated therefrom.

In a specific embodiment, the electrical current may be measured using measuring device being a current transformer or a Hall effect current sensor. Both, the current transformer and the Hall effect current sensor may measure the electric current in a conductor arrangement without physical contact. For example, a secondary winding of a current transformer may be arranged adjacent to the, or surrounding the conductor arrangement in which the electrical current to be measured flows such that changes in the electrical current induce an electrical current within the secondary winding. Accordingly, the electrical current in the conductor arrangement may be measured by measuring the current in the secondary winding and thus without having direct electric contact to the conductor arrangement.

According to an embodiment, the measuring device, i.e. the current transformer (CT) or the Hall effect current sensor, is arranged at the multi-phase alternating current circuitry or at the neutral wire connected in parallel to such circuitry. In this context, "arranged" shall mean that the measuring device is arranged close enough to the multi-phase alternating current circuitry or at the neutral wire such that the indicator current flowing through one of these components may be measured without contact by e.g. inductive coupling.

For example, a ring forming the secondary winding of the current transformer may enclose all legs of the multi-phase alternating current circuitry such that the net sum of all phases of the multi-phase alternating current transmitted through this circuitry may be measured. In such arrangement, a single secondary winding arrangement may enclose all legs of the multi-phase alternating current circuitry. Alternatively, the secondary winding arrangement of the current transformer may comprise several separate sub-winding arrangements, each sub-winding arrangement enclosing one of the legs of the multi-phase alternating current circuitry.

Alternatively, a secondary winding of the current transformer may enclose the neutral wire. As a current is induced in this neutral wire upon any changes in the phase relationship between phases of the multi-phase alternating current flowing through the various legs of the multi-phase alternating current circuitry, arranging the current transformer at the neutral wire by for example enclosing the neutral wire with the secondary winding of the CT may enable measuring an electric indicator current which is indicating any changes in the phase relationships in the multi-phase alternating current circuitry.

According to an embodiment, the multi-phase alternating current circuitry is provided in a Wye-configuration. Such Wye-configuration is sometimes also referred to as Y-configuration or star-configuration.

A Wye-configuration for the multi-phase alternating current circuitry may be beneficial as it may provide for common neutral points on a supply side and on a load side of the multi-phase alternating current circuitry such that a neutral wire may be provided by connecting to these neutral points. At such neutral wire, the electric indicator current may be measured particularly easily.

However, it is to be noted that three-phase alternating current circuitry may be configured in either, a Wye-configuration or a delta-configuration (Δ-configuration) and that any Wye-configuration may be reconfigured to result in a delta-configuration, and vice versa. It is also to be noted that multi-phase alternating circuits may be arranged with any number of phase circuit legs or branches, where electrical power is applied to each phase circuit branch and where the alternating voltage applied across each phase circuit branch may also have a phase-angle that differs between them at any moment in time.

According to an embodiment, the neutral wire is connected between common points of a supply side of the multi-phase alternating current circuitry and a load side of the multi-phase alternating current circuitry, respectively. In a neutral wire connected to such common points at the supply side and at the load side, an electric current flowing through the neutral wire will vary upon any change of a phase relationship of multiple phases of currents flowing through the various legs of the multi-phase alternating current circuitry. In multi-phase power generation systems, current flowing between the neutral point of the multi-phase power source and the neutral point of the electrical loads of each phase is commonly called the unbalanced load current.

According to an embodiment, each of the phases of the multi-phase alternating current is applied to at least one of the cords of the suspension member.

In other words, preferably none of the phases of the multi-phase alternating current is directed through a separate resistor only, this separate resistor not forming part of the suspension member. Instead, it may be preferable to transfer each of the phases of the multi-phase alternating current at least partially to one of the cords of the one or more suspension members of suspension member arrangement.

Accordingly, in such arrangement, for example temperature variations resulting in varying electrical characteristics of the cords may not significantly alter the phase relationship of the various phases of the multi-phase alternating current through the legs of the multi-phase alternating current circuitry as each cord, and therefore each of the legs, is subject to substantially the same temperature variations such that electrical characteristics will change in a same manner in all legs and will therefore at least partially be compensated.

According to an embodiment, in an initial state before deterioration, electrical resistances within each of the legs of the multi-phase alternating current circuitry are adapted to be substantially equal.

In other words, the multi-phase alternating current circuitry and, particularly, the way in that cords of the suspension member(s) are included in such circuitry may be designed such that substantially equal electrical resistances are included in each of the legs of the multi-phase alternating current circuitry. Due to such equal resistances, initially, a balanced current distribution throughout the legs of the multi-phase alternating current circuitry may be obtained.

In case, for example, electrical resistances provided by an inclusion of one or more conductive cords of the suspension member(s) into one or more of the legs of the multi-phase alternating current circuitry significantly differ between the various legs of the circuitry, additional separate resistors may be included in one or each of the legs in order to specifically adapt a total resistance throughout the one or each of the legs.

Therein, it may be sufficient to choose such additional resistors such that the total resistance throughout each of the legs of the circuitry is substantially equal. It may be emphasized that it is not necessarily required to know absolute values of the resistances of such additional resistors but it may be sufficient to adapt the addition of such resistors such that the phases of the multi-phase alternating current are applied to the cords, or to the legs comprising the cords, respectively, in an evenly distributed manner.

With such an initial state and phases of the multi-phase alternating current being distributed evenly throughout the various legs of the multi-phase alternating current circuitry, an initial configuration may be obtained in which the net sum current of all phases of the multi-phase alternating current as well as a potential electric bypass current through a neutral wire will be substantially zero. Accordingly, when repeatedly measuring one of these indicator currents during subsequent operation of the elevator, any deviation of the indicator current value from such initial zero value may easily indicate a change in the phase relationship between the phases throughout the legs of the circuitry and therefore a change in the deterioration state of the suspension member arrangement.

According to an embodiment, several cords of the suspension member are connected in a parallel arrangement and/or in a series arrangement or a combination of the two. In other words, several cords of a same suspension member, or between cords of different suspension members, may be connected in parallel with each other, may be connected in series to each other or some cords are connected in series to each other and some of such series connection are connected in parallel to each other. Each of the parallel or series arrangements or combinations thereof may have its own advantages, as described in further detail below.

According to a further embodiment, the suspension member arrangement comprises a plurality of suspension members and cords of one suspension member are connected in a parallel arrangement and/or in a series arrangement to cords of another suspension member. Again, both, the parallel arrangement and the series arrangement or a combination thereof may have its own specific advantages as described in further detail below.

According to an embodiment, the phases of the multi-phase alternating current are supplied with an even phase offset from each other. For example, the multi-phase alternating current may comprise two phases offset from each other by 180°. In another example, the multi-phase alternating current may comprise three phases offset from each other by 120°. An even offset between the phases of the multi-phase alternating current may contribute to a balanced current distribution throughout the legs of the multi-phase alternating current circuitry.

According to a second aspect of the present invention, a device for detecting a deterioration state of a load bearing capacity in a suspension member arrangement for an elevator is described. The suspension member arrangement may be configured as described above with respect to the first aspect of the invention. The device is configured to perform a method according to an embodiment as described above with respect to the first aspect of the invention.

According to an embodiment, the device comprises a multi-phase alternating current circuitry, a connector arrangement, a measuring arrangement and a determination arrangement. The multi-phase alternating current circuitry comprises multiple legs. Each leg comprises an alternating current voltage supply such as to apply each of multiple phases of a multi-phase alternating current to one of the legs. The connector arrangement is adapted for electrically connecting the multi-phase alternating current circuitry to the suspension member such that at least one phase of the multi-phase alternating current is applied to at least one of the cords of the suspension member and such that at least one other phase of the multi-phase alternating current is applied to another at least one cord of the same or another suspension member and/or to one or more separate resistors. The measuring arrangement is configured for measuring an electric indicator current being a net sum of all phases of the multi-phase alternating current and/or an electric bypass current through a neutral wire being connected in parallel to the multi-phase alternating current circuitry. The determination arrangement is adapted for determining the deterioration state based on the measured electric indicator current.

According to an embodiment, the measuring arrangement may comprise a measuring device for contactless measuring of an electric current in a conductor arrangement. For example, such measuring device may be a current transformer or a Hall effect current sensor. Particularly, the measuring device may be adapted for measuring the electrical indicator current within the multi-phase alternating current circuitry and/or its neutral wire inductively.

A further aspect of the present invention relates to an elevator comprising a device as described according to an embodiment of the above-described second aspect of the invention.

It shall be noted that possible features and advantages of embodiments of the invention are described herein partly with respect to a method for detecting a deterioration state in a load bearing capacity of a suspension member and partly with respect to a device which is adapted for performing or controlling such method in an elevator. One skilled in the art will recognize that the features may be suitably transferred from one embodiment to another, i.e. from the method to the device or vice versa, and features may be modified, adapted, combined and/or replaced, etc. in order to come to further embodiments of the invention.

DESCRIPTION OF THE DRAWINGS

In the following, advantageous embodiments of the invention will be described with reference to the drawings. However, neither the drawings nor the description shall be interpreted as limiting the invention.

The figures are only schematic representations and are not to scale. Same reference signs refer to same or similar features throughout the figures.

DETAILED DESCRIPTION

Figure 1:
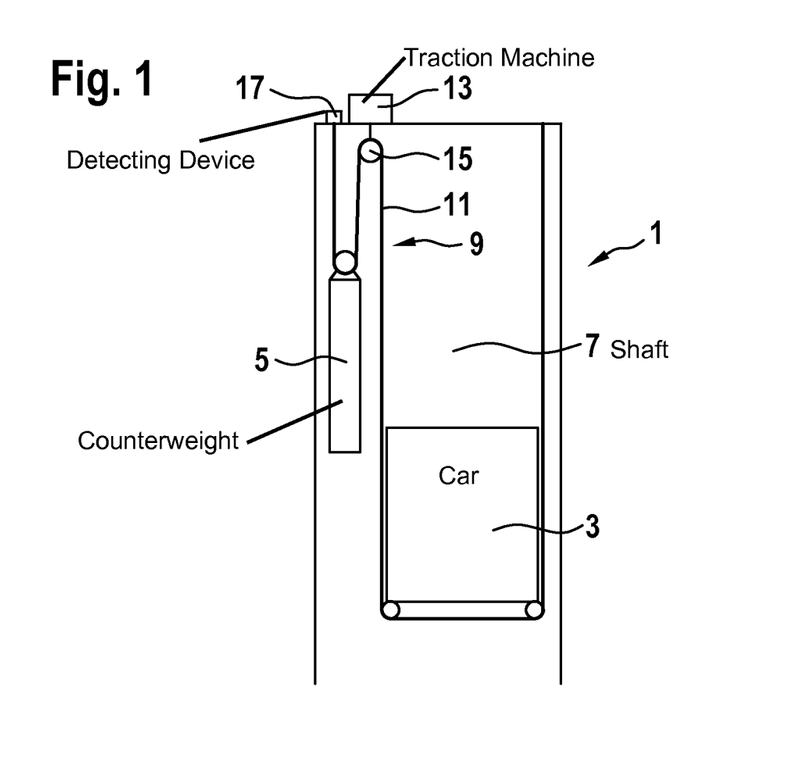
FIG. 1 shows an elevator in which a method and device according to an embodiment of the invention may be applied.

FIG. 1 shows an elevator 1 in which the method and/or device according to embodiments of the present invention may be implemented.

The elevator 1 comprises a car 3 and a counterweight 5 which may be displaced vertically within an elevator shaft 7. The car 3 and the counterweight 5 are suspended by a suspension member arrangement 9. This suspension member arrangement 9 comprises one or more suspension members 11. Such suspension members 11 may be for example ropes, belts, etc. In the arrangement shown in FIG. 1, end portions of the suspension members 11 are fixed to a supporting structure of the elevator 1 at a top of the elevator shaft 7. The suspension members 11 may be displaced using an elevator traction machine 13 driving a traction sheave 15. For example, at one end portion of the suspension member arrangement 9, a device 17 for detecting a deterioration state of a load bearing capacity in the suspension member arrangement 9 may be provided.

It may be noted that the elevator 1 and particularly its suspension member(s) 11 and its device 17 for detecting the deterioration may be configured and arranged in various other ways than those shown in FIG. 1.

Suspension members 11 to be driven for example by the traction machine 13 may utilize metal cords or ropes to support a suspended load such as the car 3 and/or the counterweight that is moved by the machine 13.

Figure 2:
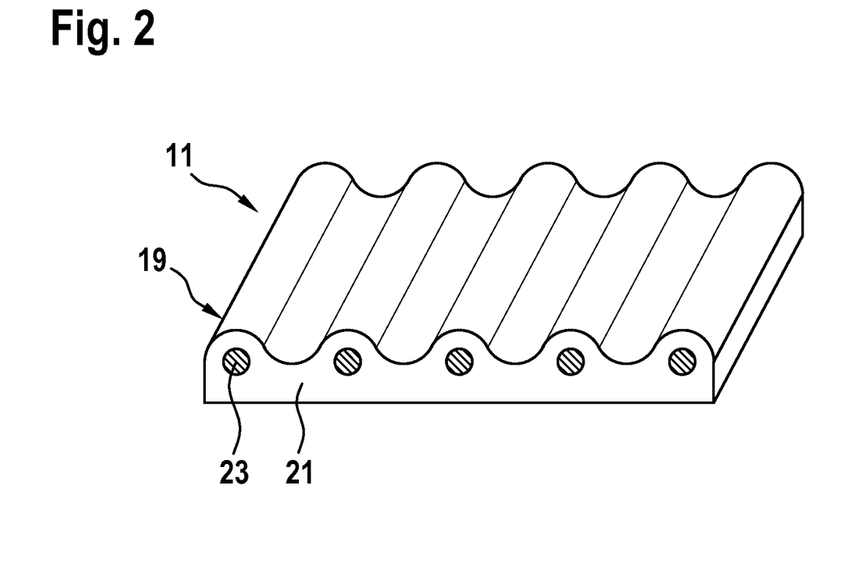
FIG. 2 shows a suspension member.

FIG. 2 shows an example of a suspension member 11 which is embodied with a belt 19. The belt 19 comprises a plurality of cords 23 which are arranged parallel and spaced to each other. The cords 23 are enclosed in a matrix material 21 forming, inter alia, a coating. The cords 23 may typically consist of or comprise metal such as steel. The matrix material 21 may typically consist of or comprises a plastic or elastomeric material. Accordingly, the cords 23 are typically electrically conductive such that an electric current can be fed through the cords without significant losses. Furthermore, the cords are preferably electrically isolated from each other via the interposed matrix material 21 which is electrically insulating such that an electrical current between neighbouring cords cannot be transmitted, i.e. no significant shunt current can flow from one cord to another.

Alternatively, suspension members 11 may have other shapes or configuration. For example, a belt may have several cords included into a body formed of matrix material, the body being non-profiled (i.e. flat) or having other shapes as those shown in FIG. 2. Alternatively, each cord may be enclosed by matrix material forming a kind of coating wherein the coated cords are separate from each other, i.e. not connected to each other via common matrix material. Generally, the suspension members 11 may be provided as coated steel suspension members.

Typically, wires or cords of the suspension member 11 have a specified minimum strength to ensure an integrity of the suspension member arrangement 9 during its use in an application within an elevator 1. In certain suspension applications, such as for lifts or elevators, a factor-of-safety requirement for strength combined with other measures, such as protective coating of the cords 23 for example within the matrix material 21, may sustain an initial strength of a suspension member beyond an effective life of the protective measures employed to retain strength.

Particularly in such cases, where the initial strength of the suspension member 11 is not expected to change during its useful life in an application, a simple electronic method may be employed and may be sufficient to detect an indication that for example initial physical properties of the suspension members have unexpectedly changed and trigger for example a replacement of the suspension member 11.

PRIOR ART APPROACHES—In prior art, methods have been employed to ensure that suspension members do not fall below a specified minimum strength, such methods involving for example visually counting of broken wires of cords or wire rope strands over a length of the suspension members. Alternatively, complex electronic methods that measure small changes in an electrical resistance of for example metal cords and compare such measurements with reference values or a rate of change in resistance have been proposed.

Although such methods may be effective, they may have certain disadvantages. For example, counting broken wires may be a tedious task periodically performed by persons maintaining the suspension members of an elevator and may be flawed by human error. In cases where suspension members have an opaque coating on the metal cords or the metal cords are incorporated into a matrix material, it is generally not possible to visually count broken wires. Where methods employ monitoring a change in electrical resistance or impedance of metal cords, the measurements are generally made across electrical connections to the steel cords and may introduce, by nature of such electrical connections, a significant source of possible errors due to for example very low electrical values of resistances being monitored. Furthermore, over time, such electrical connections may deteriorate due to effects of e.g. oxidation and/or contamination and may increase a potential for errors by the monitoring method. Additionally, such methods typically involve complex circuits necessary for measuring the very small changes in resistance or impedance and comparing them for example to target reference resistance values that may drift over time or due to effects of temperature. Furthermore, some prior art approaches may require extensive correlation to map a change in resistance or impedance of the steel cords with changes in a strength and/or physical deterioration of the steel cord.

NEW APPROACH—Accordingly, there may be a need for a less complex and/or more effective monitoring method for detecting a deterioration in suspension members, particularly, in case these suspension members are expected to retain their initial strength over the life of their application.

As described herein, a simple and reliable method may be achieved using a multi-phase current monitoring of e.g. steel cords in a suspension member where only a significant change in initial physical conditions of the cords need to be monitored. Such method may also be useful for monitoring one or more physical properties related to both the strength of the cords and the electrical conductivity of the cords, such as the cords cross sectional area, and/or with correlated data, if available.

In other words, an aim of embodiments of this invention may be to provide a novel and improved method for monitoring physical characteristics of e.g. electrically conductive steel cords in a suspension member in order to thereby detect a deterioration state of a load bearing capacity of the suspension member. Based on such monitoring, a suspension member may be replaced or retired when an allowable deterioration is exceeded. In such monitoring or detecting procedure, electronic measurements are performed that are related to electro-physical characteristics of cords comprised in a suspension member arrangement.

Ideas underlying embodiments of the invention may provide for various advantages or characteristics. For example, such ideas do not necessarily require correlation of physical changes in the cords with electronic measurements to establish target values to retire a suspension member. Furthermore, no elaborate signals are necessarily required to be transmitted and monitored at physical connections to the cords. Retirement criteria for the suspension members may be based on a change in an initial electronic measurement for example of a net sum of a multi-phase current applied to the cord circuit arrangement of the suspension member. All initial electrical conditions established with the power applied to the cords, and related electrical loads in both circuits may be taken into account. Measurements of a net sum of the multi-phase alternating current in the multi-phase alternating current circuitry comprising cords of the suspension members in at least one of its legs may be sensed for example without direct electrical connection, for example by using a current transformer that is located with a monitoring electronics and/or a processor. The method may take benefit of characteristics of the multi-phase alternating current circuitry comprised therein, such multi-phase alternating current circuitry enabling compensation of changes in temperature for example. Furthermore, a correlation between electro-physical characteristics of cords of the suspension members and the electronic measurement applied in the detection method according to embodiments of the present invention may also be used to discern gradual or incremental physical changes in the cords of the suspension members to trigger action for preparation and eventual retirement of the suspension members.

Following hereto, possible details and features of the method and the device according to embodiments of the present invention will be given.

MULTI-PHASE ALTERNATING CURRENT CIRCUITRY—The multi-phase alternating current circuitry includes multiple electrically conductive legs. The circuitry comprises a source side with voltage sources and a load side with resistances and/or impedances. As used herein, "alternating current" shall mean a non-constant current, i.e. a current strength or amperage varies over time. Particularly, the current may vary periodically and, more particularly, may periodically reverse its direction. Furthermore, "multi" shall mean "at least two". I.e. the circuitry may comprise 2, 3, 4 or more electrically conductive legs. A "leg" may comprise an electrically conductive line or conductor connecting the source side of the circuitry with the load side thereof. Furthermore, a leg may comprise one or more electrical devices, particularly resistances or impedances, included in series with the line or conductor.

The multi-phase alternating current circuitry may be adapted such that multiple phases of a multi-phase alternating current may be directed through each of the legs of the multi-phase alternating current circuitry. For such purpose, the circuitry generally comprises multiple voltage sources, one voltage source being comprised in each of the legs and being adapted to apply an alternating voltage to an electrically conductive line within the respective leg. Furthermore, the circuitry generally comprises electrical resistances which may be generated by the resistivity of the electrically conductive line itself and/or by resistors comprised in the respective leg.

Figure 3:
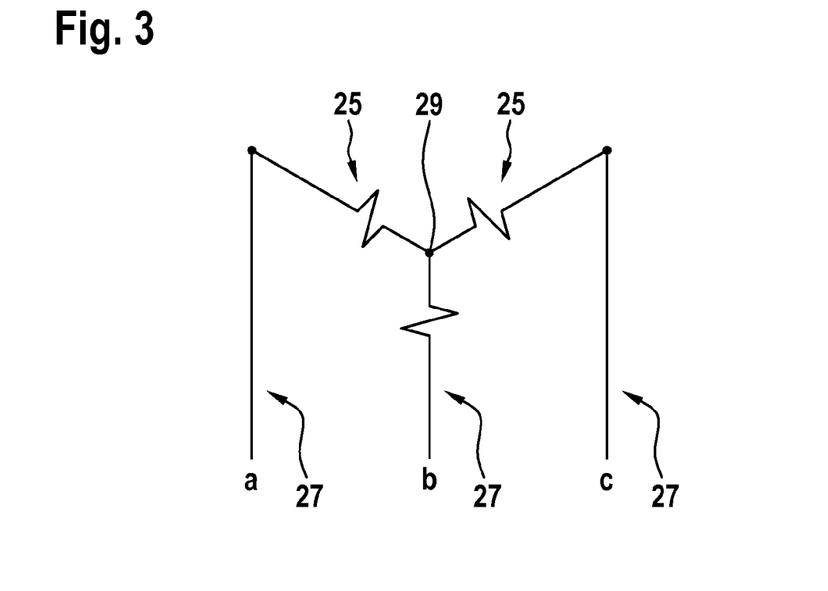
FIG. 3 shows a Wye-configuration of a circuitry.
Figure 4:
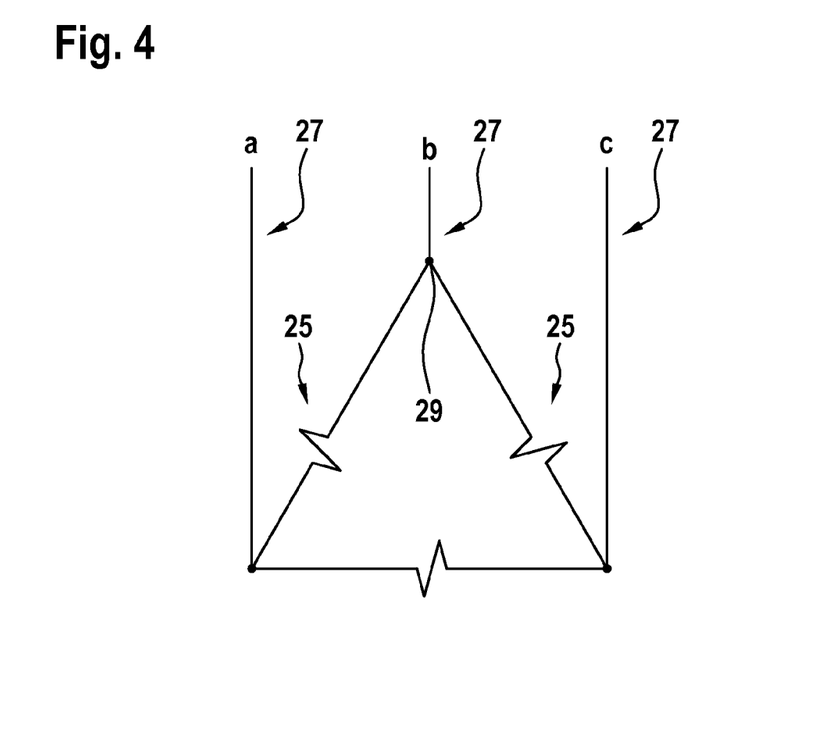
FIG. 4 shows a Delta-configuration of a circuitry.

FIG. 3 shows schematically a Wye-configuration of a portion of a multi-phase alternating current circuitry. FIG. 4 shows a Delta-configuration. The configurations include electrical components 25. Such components 25 may be various electrical elements, depending for example on whether the circuit configuration shall be a source or a load. For example, in a source, the components 25 may be voltage sources. In a load, the components 25 may be electrical resistors. In the Wye-configuration, multiple electrical components 25 are connected such that one side of each of the electrical components 25 of the Wye-configuration is connected to a common point 29 whereas an opposite side of the electrical component 25 is connected to one of the lines a, b, c forming legs 27 of the circuitry. In the Delta-configuration, the electrical components 25 are connected serially in a ring-like manner and each of the lines a, b, c forming the legs 27 of the circuitry is connected in between of two neighbouring electrical components 25.

It shall be noted that, while embodiments of the invention are described herein with reference to an example having three phases, i.e. being implemented with a three-phase alternating current circuitry, other numbers of phases such as for example two phases, four phases or more phases may be applied when implementing embodiments of the invention.

Figure 5:
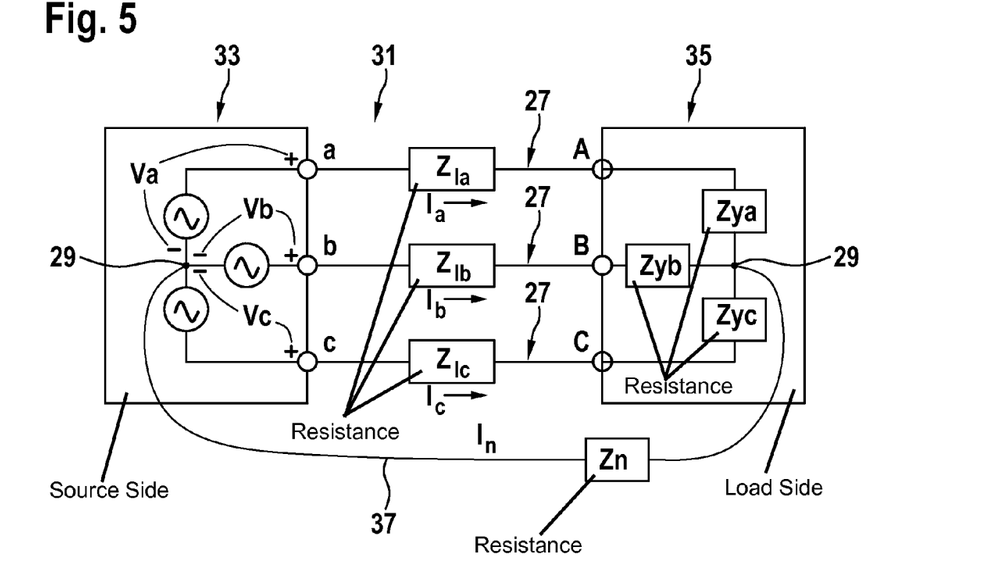
FIG. 5 shows an example of a multi-phase alternating current circuitry.

FIG. 5 shows an example of a multi-phase alternating current circuitry 31 comprising three electrically conductive legs 27 wherein both, a source side 33 and a load side 35 are configured in a Wye-configuration. Alternating voltage sources Va, Vb, Vc are provided in a Wye-configuration at the source side 33. Resistors Zya, Zyb, Zyc are provided in a Wye-configuration at the load side 35. Both Wye-configurations have a neutral point 29 at which the voltage sources Va, Vb, Vc or the resistors Zya, Zyb, Zyc, respectively, are all interconnected. The alternating voltage sources Va, Vb, Vc are connected via the lines a, b, c forming the legs 27 to associated ones of the resistors Zya, Zyb, Zyc. Accordingly, current phases $I_a$, $I_b$, $I_c$ of a multi-phase alternating current may be applied to each line a, b, c of the legs 27.

Furthermore, in the exemplary multi-phase alternating current circuitry 31 of FIG. 5, a neutral wire 37 is connected to each of the neutral points 29 at the Wye-configuration at the source side 33 and the Wye-configuration at the load side 35. In other words, the neutral wire 37 is connected between the common points 29 of the supply side and the load side of the multi-phase alternating current circuitry, respectively. The neutral wire 37 comprises a resistance Zn. In the neutral wire, a bypass current $I_n$ may flow.

MULTI-PHASE ALTERNATING CURRENT—A multi-phase alternating current comprises at least two phases wherein in each phase the current alternates over time. There is a phase-shift between the phases such that for example a peak current strength in one phase is shifted by $2\pi/n$ (n=2, 3, 4, ...) with respect to a peak current strength of another phase. The currents may alternate for example in a sinusoidal manner. However, also other alternation patterns, such as digital, stepwise, or others, may be applied.

Figure 6:
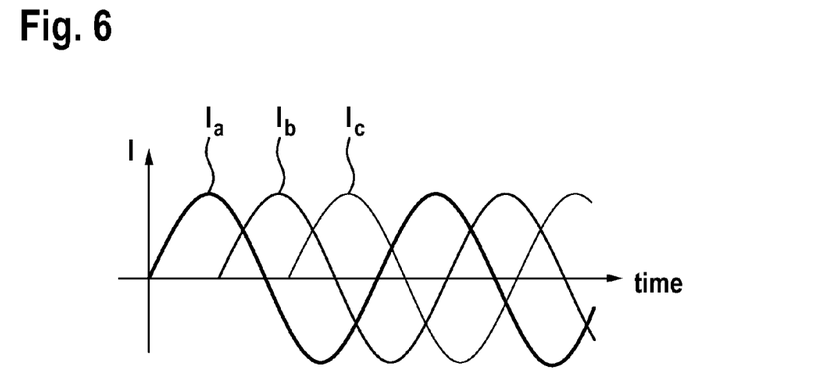
FIG. 6 visualizes phases of a multi-phase alternating current.

In other words and in the example of three phases, in electrical circuit design, three-phase electric circuits generally have three conductors for example formed by lines a, b, c carrying voltage waveforms that are $2\pi/3$ radians (i.e. 120° or ⅓ of a cycle) offset in time as shown in FIG. 6.

MEASURING THE INDICATOR CURRENT—Where the three conductors carrying the voltage waveforms are "balanced", a net sum of phase currents throughout all legs 27 of the multi-phase alternating current circuitry 31, i.e. a vector sum of $I_a$, $I_b$, $I_c$ is 0 (i.e. $I_a+I_b+I_c=0$, wherein $I_a$, $I_b$, $I_c$ shall be vector currents and thus include information about their phases). In a balanced three-phase circuit, all three sources Va, Vb, Vc are generally represented by a set of balanced three-phase variables and all loads Zya, Zyb, Zyc as well as lines a, b, c within the legs 27 of the circuitry have equal impedances. Furthermore, in such balanced circuit, not only the net sum of the phase currents is 0, but also an electric bypass current $I_n$ through the neutral wire 37 being connected in parallel to the legs 27 is 0 (i.e. $I_n=0$).

Following Kirchhoff's voltage law, when there is an imbalance in the conductor loads of the three-phase circuit, any resulting imbalance of phase currents in the legs 27 of the circuitry 31 will be resolved as a current $I_n$ in the neutral wire 37 and/or as a net sum phase current throughout all phases a, b, c of the multi-phase alternating current being no more equal to 0.

Such deviation of the bypass current $I_n$ through the neutral wire 37 or of the net sum of all other phase currents $I_a$, $I_b$, $I_c$ may be interpreted and named herein as "electric indicator current". As soon as this indicator current deviates from a reference current value by more than a predetermined difference value, this may be taken as signal indicating that critical deterioration has occurred within at least one of the suspension members and checking and, if necessary, replacing the suspension member may be initiated for example. The reference current value may be, for example a current value of the bypass current $I_n$ or a net sum of the phase currents $I_a$, $I_b$, $I_c$ measured with a non-deteriorated suspension member arrangement such as for example directly after fabrication or installation of a suspension member arrangement.

The indicator current may be measured in various ways. For example, a vector net sum of all currents $I_a$, $I_b$, $I_c$ throughout all of the legs 27 of the multi-phase alternating current circuitry 31 may be measured together, i.e. with a common measuring circuitry. Alternatively, each of the phase currents $I_a$, $I_b$, $I_c$ in the lines a, b, c forming the legs 27 may be measured separately and a net sum of these separately measured phase currents may then be determined subsequently, for example in a summing device. Alternatively, the indicator current may be derived from the bypass current $I_n$ flowing through the neutral wire 37 upon any imbalance within the multi-phase alternating current circuitry 31.

For example, with reference to the circuitry 31 shown in FIG. 5, voltages Va, Vb, Vc are applied to lines a, b, c forming the legs 27 and are held constant, i.e. equal to each other, and $2\pi/3$ radians shifted apart. At least one of the lines a, b, c may comprise at least one of the cords comprised in a suspension member of the suspension member arrangement of the elevator. For a net sum $(I_a+I_b+I_c)$ and/or a bypass current $I_n$ in the neutral wire 37 to be equal to 0 under initial conditions, such as when the suspension member is newly installed, voltage drops across each of the lines a, b, c plus voltage drops across each of the loads Zya, Zyb, Zyc in each of the legs 27 must be equal.

In practical terms, the voltage drops across for example steel cords in a suspension member will not necessarily be initially equal due to for example various small differences and tolerances created by for example manufacturing tolerances of the steel cords in the suspension member. In this case, the loads Zya, Zyb and Zyc may be adjusted to compensate for such differences until a desired initial current condition for $I_n=0$, i.e. no current flow in the neutral wire, is obtained. Alternatively the multi phase source voltages Va, Vb, Vc on the source side 33 may be independently adjusted to likewise establish a desired initial current condition for $I_n$. Intuitively for those skilled in the art, an alternative to adjusting the loads Zya, Zyb, Zyc and/or the multi phase source voltages Va, Vb, Vc for an initial zero $I_n$ current would be to capture a non-zero value of $I_n$ as the initial reference current value.

Suspension members that contain multiple metal cords are generally capable of having the cords acting as electrical conductors or lines. The suspension member may also be construed with metal cords that are isolated electrically from each other by a physical separation, such as with electrically non-conductive materials like an elastomeric coating. Where the metal cords in suspension members are electrically isolated from each other, they may be connected for example in a Wye-configuration or a Delta-configuration and be part of various legs of a multi-phase alternating current circuitry. Each of the cords may then become an electrical conductor in the circuitry.

For example, in the Wye-configuration of FIG. 5, three isolated cords in a suspension member are represented by $Z_{1a}$, $Z_{1b}$, $Z_{1c}$. In an initially balanced state, the sums of resistances $Z_{1x}+Zyx$ (x=a, b, c) in each of the lines a, b, c formed by the cords are substantially equal. However, upon deterioration of one of the cords, the resistance $Z_{1x}$ created thereby in one of the lines changes and the entire multi-phase alternating current circuitry 31 comes into imbalance. Such imbalance may then be determined by measuring the indicator current $I_n$ or $(I_a+I_b+I_c)$. If this indicator current exceeds a certain predetermined value, this may be taken as indication that at least one of the cords comprised in a suspension member is significantly deteriorated and the suspension member may have to be checked and/or replaced.

Instead of forming all lines a, b, c or, more generally, all legs 27 of a multi-phase alternating current circuitry 31 by including one of the cords of a suspension member, for example only one or a few of those lines may include cords of the suspension member. For example, as described further below with respect to various examples, all cords of a suspension member or of plural suspension members may be connected in series or in parallel and may be included into only one of the legs 27 whereas the other legs 27 do not comprise any cords but are formed only with the loads Zyx. These loads Zyx may be fixed or dynamic. For example, dynamic loads may be implemented for setting up initial conditions for $I_n$ and/or compensating any temperature effects modifying electrical characteristics in the loads Zyx, the lines a, b, c, the cords comprised in the multi-phase circuitry and/or other components of the multi-phase circuitry.

It may be noted that setting up initial conditions for $I_n$ and/or compensating for the effects of temperature or other phenomena may also be accomplished by dynamically adjusting the loads Zya, Zyb, Zyc and/or the multi phase source voltages Va, Vb, Vc.

CONTACTLESS MEASUREMENT OF THE INDICATOR CURRENT—In one preferred embodiment, the indicator current is measured in a contactless manner. For such contactless measuring, a measuring arrangement comprising a measuring device for contactless measuring of an electrical current in a conductor arrangement may be used. Preferably, a current transformer (CT) may be used for such contactless measuring. Alternatively, a Hall effect current sensor may be used.

For example, when an electric current passes through a line, this current creates both a voltage drop across such line and a magnetic field. The magnetic field can be used to sense a magnitude and direction of the current in the conducting line. Both, a voltage drop and the magnetic field are created by electro-physical characteristics of the line. Accordingly, if one or all of the lines forming legs of a multi-phase alternating current circuitry comprise at least one of the cords of a suspension member, the voltage drop there through and the magnetic field created thereby upon phase current application allows deriving information about physical properties of the cord. These characteristics are, at least in part, generally dependent upon the same physical properties of the cord that also determine the strength of the cord, such as for example the cord diameter. The magnetic field around a conductor is generally directly proportional to the current flowing in it.

Accordingly, any wireless measuring device which may measure changes in the magnetic field generated by changes in currents flowing through a conductor may be used for contactless measuring the current flow through the conductor.

A current transformer is an example for one of such measuring devices. A current transformer typically comprises windings or coils which serve as secondary windings. These windings may be mounted on a core made e.g. from ferrite or iron. The windings may be used to couple by induction with the magnetic field generated by the current flowing through one or more of the lines of the multi-phase alternating current circuitry which, in such case, act as primary winding(s). An output at the secondary winding(s) is generally proportional to the current through the primary winding(s). An operation of such CT is in principle substantially identical to that of any step-up transformer or step-down transformer. A number of secondary windings and their geometry may be adapted to the current(s) to be measured, particularly to a magnitude, a frequency, phase relationships, etc. of such currents. Furthermore, the number of secondary windings may be adapted in order to obtain a desired output which may be easily measured and analysed. Generally, the number Ns of secondary windings determines a transformation ratio which directly depends on a ratio Ns/Np of the number Ns of secondary windings to a number Np of primary windings.

The CT may be provided with various geometries, circuitries, etc. and may be provided with a same or similar design like conventional transformers such as step-up transformers, step-down transformers, Rogowski transformers, etc. The windings of the CT may be arranged in an open loop or in a closed loop.

Measuring currents wirelessly, particularly measuring currents using a CT, may provide for a number of advantages, especially when applied to measurements of an indicator current in embodiments of the method described herein.

For example, such measuring methods allow for voltage isolation between the circuitry in which the current to be measured flows and a circuitry of the measuring device. Such voltage isolation may be particularly beneficial in case installation or monitoring personal shall measure indicator currents within a suspension member arrangement of an elevator as such personal can then be suitably protected against any direct contact if relatively high voltages are applied to the suspension member arrangement.

Furthermore, no direct ohmic contacts between the measurement circuit and the circuitry in which the current to be measured flows have to be established. This may save work efforts and material costs. Furthermore, such ohmic contact may otherwise frequently cause long-term problems such as corrosion, contact losses, etc.

Additional advantages may be typically low cost of contactless measuring devices, such as a CT, and their high reliability. Furthermore, no external power supplies are required for such measuring devices. Additionally, such measuring devices are particularly beneficial in noisy environments as a current output is provided which may then be easily converted into a voltage output.

Particularly when applied to embodiments of the method described herein, using contactless measurement devices such as a CT may enable simple, safe, reliable and/or cost effective measuring of the indicator current as e.g. no direct physical and/or electrical access to suspension members, particularly to the cords comprised in the suspension member is necessary.

Figure 7:
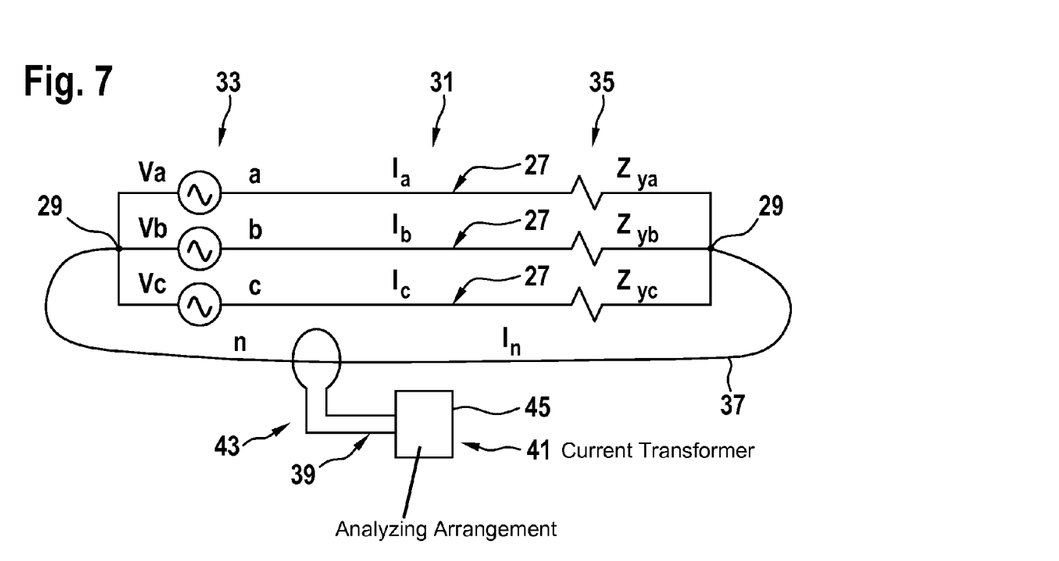
FIG. 7 shows a first example of an arrangement for measuring an indicator current in a multi-phase alternating current circuitry without physical contacts in the circuit to make the indicator current measurement.
Figure 8:
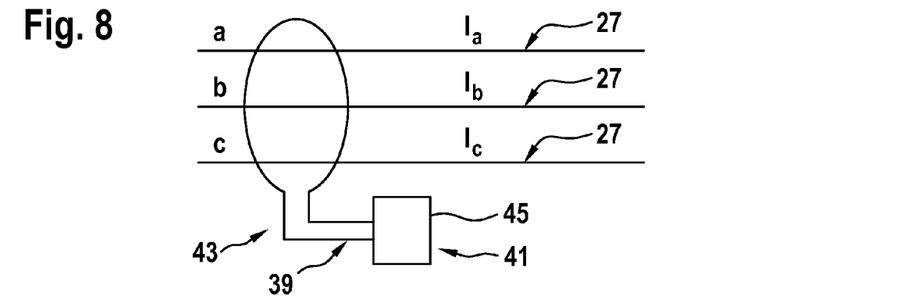
FIG. 8 shows a second example of an arrangement for measuring an indicator current in a multi-phase alternating current circuitry without physical contacts in the circuit to make the indicator current measurement.
Figure 9:
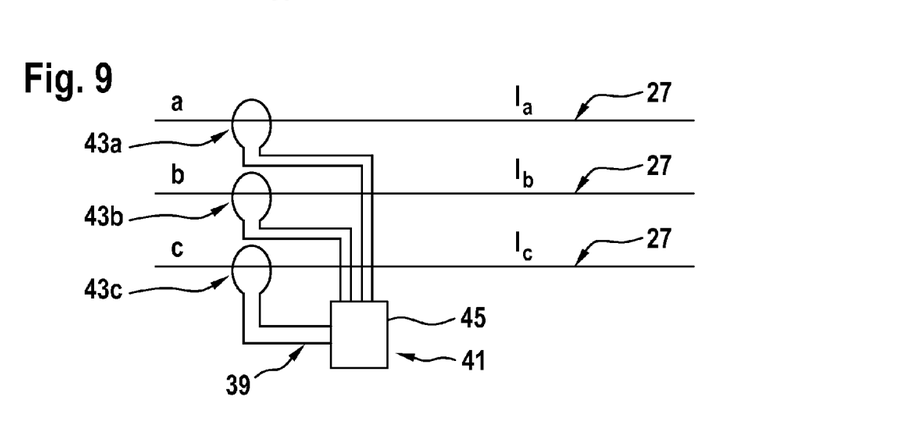
FIG. 9 shows a third example of an arrangement for measuring an indicator current in a multi-phase alternating current circuitry without physical contacts in the circuit to make the indicator current measurement.

FIGS. 7, 8, 9 show alternatives of measuring arrangements for measuring an indicator current in a multi-phase alternating current circuitry 31 for application in the method according to embodiments of the present invention.

FIG. 7 shows a multi-phase alternating current circuitry 31 similar to that one of FIG. 5. Voltage sources Va, Vb, Vc are provided on a source side 33 and loads Zya, Zyb, Zyc are provided on a load side 35. Both, the source side 33 and the load side 35 are provided in a Wye-configuration. Phases $I_a$, $I_b$, $I_c$ flow though each of the legs 27 of the circuitry 31. A neutral wire 37 is connected to neutral points 29 of the Wye-configurations such as to be parallel to the legs 27 of the circuitry 31.

A measurement device 39 for contactless measuring is provided external to the circuitry 31 and is arranged adjacent to the neutral wire 37. In the present example, the measurement device 39 is a current transformer 41 having a secondary winding arrangement 43 and an analyzing arrangement 45. The secondary winding arrangement 43 encloses the neutral wire 37 thereby enabling inductively measuring any changes in a bypass current $I_n$ flowing through the neutral wire 37. As the neutral wire 37 may be separate to any suspension member, it may be simple to inductively measure the bypass current $I_n$. As this bypass current $I_n$ correlates to the net sum of all phase currents through the multi-phase alternating current circuitry 31, any changes and imbalances therein may be easily detected by monitoring the bypass current. With the multi-phase supply voltages and loads in the multi-phase alternating current circuitry 31 held constant, a source of any changes or imbalances would come from changes in electro-physical characteristics of the suspension member cords included in the circuitry 31, including shorts, breaks and/or reductions in cord diameter. A current in the neutral wire 37 may be dissipated e.g. by adding a load in the neutral wire 37 or by including a power supply.

FIGS. 8 and 9 each show a portion of alternative measuring arrangements. Therein, only the legs 27 of the multi-phase alternating current circuitry 31 are depicted.

In the example of FIG. 8, a large secondary winding arrangement 43 encloses all of the lines a, b, c included in the legs 27 together. Thereby, the CT 41 is enabled to simply measure a net sum current $(I_a+I_b+I_c)$ through the multi-phase alternating current circuitry 31.

For example, in case all lines a, b, c forming the legs 27 include one or more cords of a suspension member, a single secondary winding arrangement 43 may be clamped around the suspension member such that a sum of the phase currents flowing through each of its cords may be measured altogether.

In the example of FIG. 9, several small secondary winding arrangements 43a, 43b, 43c each enclose separately one of the lines a, b, c included in the legs 27. Thereby, the CT 41 is enabled to measure each of the phase current $I_a$, $I_b$, $I_c$ separately. From such separate measurements, the analyzing arrangement 45 may derive a net sum $(I_a+I_b+I_c)$ of all currents.

For example, in case some lines a, b, c forming the legs 27 include one or more cords of a suspension member whereas some other lines a, b, c forming the legs 27 do not include one or more cords of a suspension member, some of the secondary winding arrangements 43a, 43b, 43c may be clamped around the suspension member such that the phase currents flowing through its cords may be measured whereas some others of the secondary winding arrangements 43a, 43b, 43c may not be clamped around the suspension member but around separate lines including for example separate resistors, these lines forming other legs 27 of the multi-phase alternating current circuitry 31. The analyzing arrangement 45 may then calculate the net sum $(I_a+I_b+I_c)$ of currents through all legs 27.

The analyzing arrangement 45 may comprise a monitoring unit with monitoring electronics and a processor that may evaluate the net sum multi-phase current through the circuitry 31 and/or the bypass current through the neutral wire 37.

It shall be noted that, while measuring the indicator current wirelessly e.g. with a CT, other types of current measurements may be applied in alternative approaches. For example, a resistor may be included into e.g. the neutral wire and a voltage drop at such resistor may be determined in order to derive a value of the indicator current therefrom.

WIRING AND MEASURMENT ARRANGEMENTS—FIGS. 10 to 13 show various alternatives of how to include cords 23 of suspension members 11 into a multi-phase alternating current circuitry 31 in order to enable methods in accordance with embodiments of the present invention.

Generally, cords 23 of one or more suspension member 11 may be connected to each other and to lines a, b, c of a multi-phase alternating current circuitry 31 in various ways of serial and/or parallel interconnection.

For example, if the number of cords 23 in a suspension member arrangement is identical to a number of legs 27 in the multi-phase alternating current circuitry 31, each one of the cords 23 may be included in one of the legs 27. In such configuration, altering electro-physical characteristics in one of the cords 23 may result in an imbalance in the multi-phase alternating current through the circuitry 31 such that a change in the indicator current may be measured. A deviation in the indicator current from a reference value may therefore indicate that at least one of the cords 23 is deteriorated.

Where the suspension member(s) 11 comprise more cords 23 than there are legs 27 in the circuitry 31, i.e. than there are phases in the multi-phase alternating current, various wiring arrangements between the cords 23 and legs 27 of the circuitry 31 may be made.

For example, when there are four cords 23 present and the multi-phase alternating current circuitry 31 comprises three legs 27, two of the cords 23 may be wired in series or in parallel to create one conductor from the two and may then be connected to one of the legs 27. An impedance difference between each of the combined two cords 23 to that of the single conductor cords 23 in such an arrangement may be of no consequence to the monitoring method because measuring the indicator current and using it as a reference current value may take into account any such effects of cord combinations.

One skilled in the art may envision that any combination of 3, 4, 5, 6 or more cords configured into multi-phase circuit arrangements may be possible in the monitoring method proposed herein such that power supplies and loads are all connected e.g. on one end of a suspension member 11 with connections made to the cords 23 on the opposite end of the suspension member 11 to bridge and return the power from the supply to the loads. Such configurations are shown in FIGS. 10 and 11.

Figure 10:
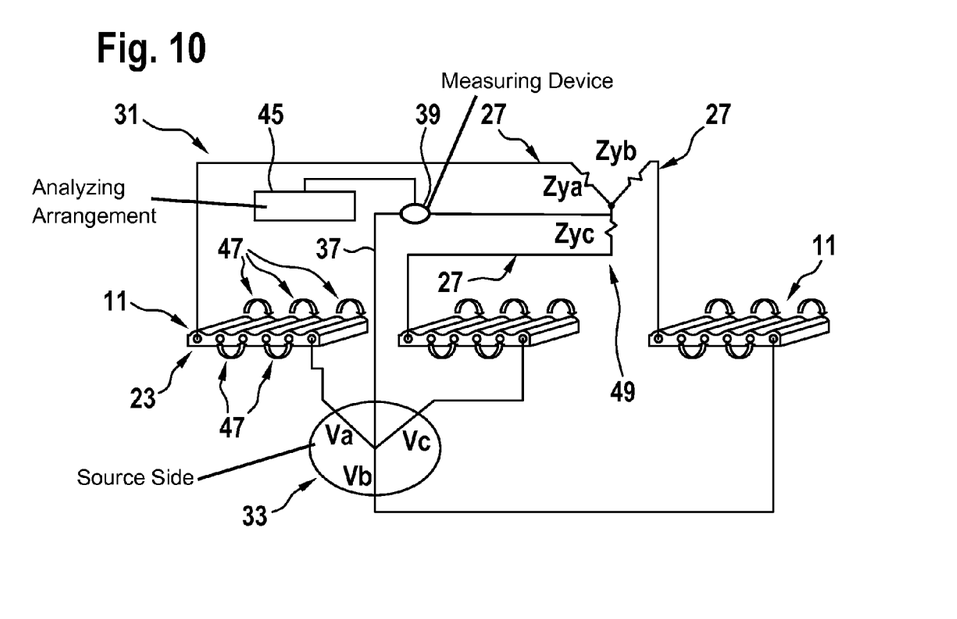
FIG. 10 shows a first example of a wiring and measuring arrangement for implementing the method or device according to embodiments of the present invention.

In the configuration of FIG. 10, a plurality of cords 23 in each of the suspension members 11 are connected in series and each suspension member 11 is included in one leg 27 of a three-phase alternating current circuitry 31. The cords 23 of one suspension member 11 are connected in series using bridge members 47 alternately arranged at opposite ends of the suspension member 11. Furthermore, optional resistive loads 49 Zya, Zyb, Zyc may be included in the Wye-configuration of the circuitry 31. Alternating voltages Va, Vb, Vc may be applied to each of the legs 27 on a supply side 33. A measuring device 39 and its analyzing arrangement 45 may be used to measure an indicator current in a neutral wire 37.

Figure 11:
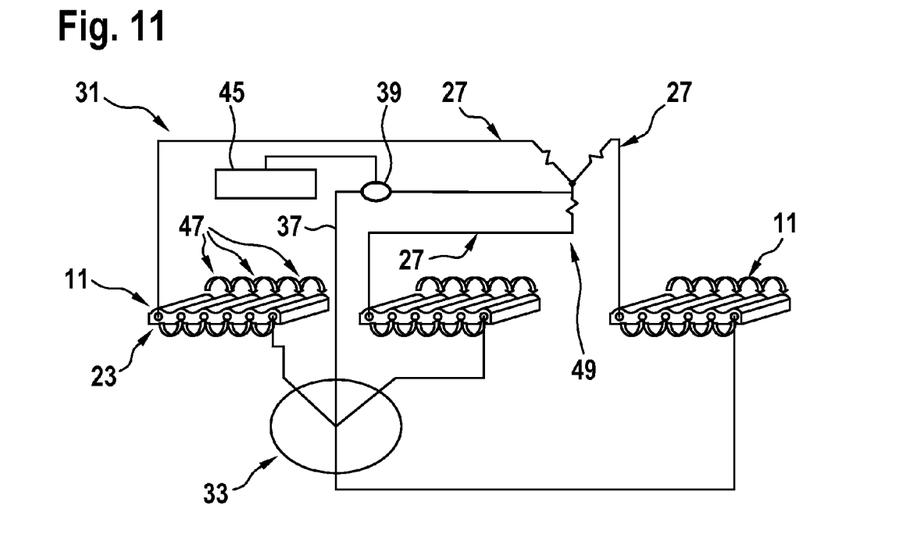
FIG. 11 shows a second example of a wiring and measuring arrangement for implementing the method or device according to embodiments of the present invention.

In the configuration of FIG. 11, a plurality of cords 23 in each of suspension members 11 are connected in parallel and each suspension member 11 is included in one leg 27 of a three-phase alternating current circuitry 31. In this case, bridge members 47 connect all cords 23 in a suspension member 11 in parallel.

Likewise, all cords 23 of multiple suspension members 11 may be connected into a single series circuit such that this series circuit is one leg 27 of the multi-phase alternating current circuitry 31 and other legs 27 constitute remaining legs 27 of the multi-phase alternating current circuitry 31 are comprised of one or more separate resistors R1, R2 forming resistive loads. Such configurations are shown in FIGS. 12 and 13.

Figure 12:
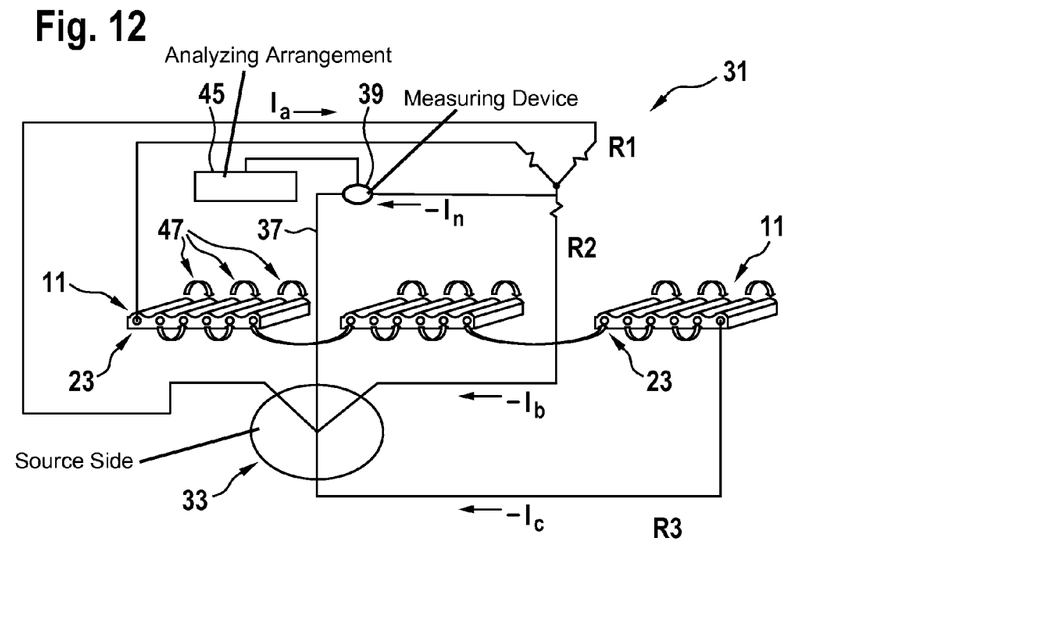
FIG. 12 shows a third example of a wiring and measuring arrangement for implementing the method or device according to embodiments of the present invention.

In the configuration of FIG. 12, a plurality of cords 23 in all suspension members 11 are connected in series using bridge elements 47 alternately arranged at opposite sides of the suspension members 23 and, altogether, are included in one leg 27 of a three-phase alternating current circuitry 31. Separate resistors R1, R2 are comprised in the remaining legs 27. A virtual resistance R3 is formed as a total resistance by all of the cords 23 in series. A measuring device 47 may be used for measuring the indicator current $I_n$ which may be for example a resulting bypass current within the neutral wire 37.

Figure 13:
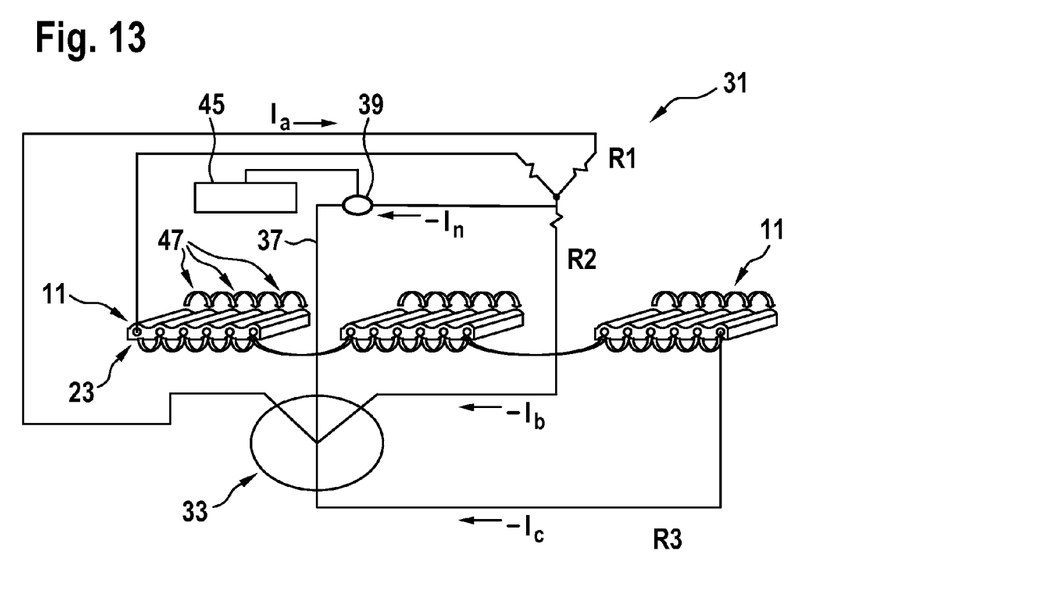
FIG. 13 shows a fourth example of a wiring and measuring arrangement for implementing the method or device according to embodiments of the present invention.

In the configuration of FIG. 13, a plurality of cords 23 in all suspension members 11 are connected in parallel using bridge members 47 within each suspension member 11 and the plurality of suspension members 11 is connected in series with each other in order to constitute one leg 27 of the three-phase alternating current circuitry 31. Separate resistors R1, R2 are comprised in the remaining legs 27. A resistance R3 is formed as a total resistance by all of the suspension members 11 in series.

Depending on how the cords 23 and suspension members 11 are interconnected and included into the multi-phase alternating current circuitry 31, different information may be derived from a measured indicator current $I_n$. For example, depending on how the various cords 23 are comprised in the circuitry 31, a change in the indicator current may indicate that electro-physical characteristics in one of the cords 23, in one of the suspension members 11 or in an entirety including all of the suspension members 11 occurred. Accordingly, in reaction to such measured change in the indicator current, counter-measures such as checking and/or exchanging one or all of the suspension members 11 of a suspension member arrangement 9 in an elevator 1 may be initiated.

EXEMPLARY CALCULATION OF EXPECTED INDICATOR CURRENT CHANGE—In the following, an exemplary result of a calculation of an expected change of an indicator current $I_n$ to be measured according to embodiments of the method described herein will be presented. It is to be noted that the assumptions, calculations and results shall be exemplary only and shall not restrict the scope of the invention in any way.

With reference to the embodiment shown in FIG. 12 having all cords 23 and all suspension members 11 connected in series, it may be calculated that, for the specific suspension member arrangement 9, changes of the indicator current resulting from substantial deterioration of a load bearing capacity may be expected due to a reduction in the cross sectional area of the cords, and can be easily measured with relatively simple measuring devices 39. Furthermore, such changes in the indicator current due to critical deterioration states may be easily distinguished from changes in the indicator current which are only due to e.g. temperature effects.

A specific calculation of a predetermined difference value by which the indicator current may change before any critical modification in the load bearing capacity of a suspension member arrangement has to be assumed, may have to take into account a wide variety of parameters such as, inter alia, a length, a diameter and/or material characteristics of the cords, a manner in which the cords are interconnected and/or connected to legs of the multi-phase alternating current circuitry in parallel and/or in series, etc.

SUMMARY REMARKS—Without restricting the invention as defined in the claims in any way, aspects of embodiments of the invention may be summarized in an alternative wording to that used in the claims as follows:

1.) Some prior art approaches require electrical measurement of resistances or impedances to detect a change in a cross sectional area and strength of the cords.

Embodiments of the method described herein do not require any measurement of resistance or impedance. Only a change in a net sum of a current flow in a multi-phase (i.e. polyphase) circuit, which is a vector sum of currents in conductors supplied by a multi-phase power source, is required. Load resistances 35 and/or multi phase source voltages 33 may be selected and incorporated for the purpose of multi-phase circuit design and may be adjusted or dynamic for other functional purposes such as load balancing, but resistance is generally not monitored or measured for the purpose of comparison with changes in resistance in the steel cords or for relating resistance (or impedance) of the cords to a change in the physical properties (e.g. a cross sectional area) of the steel cords in the suspension.

As advantages, for example a change in physical characteristics of the steel cords is proportional to a change in the net sum of the phase current and therefore can be derived from the change in the net sum of the phase current. No measurement of resistances is required to measure a change in the net sum phase currents. The steel cords can be arranged in any manner as "phase conductors" and loads in the multi-phase circuits. The measurements can be made "continuous" for monitoring a change in the electro-physical characteristics of the steel cords. Furthermore, the measurements do not require a use of a "test signal" in the cords for detecting a change in the electrical or physical characteristics of the steel cords.

As for further possible advantages, manual and/or dynamically adjusted load resistors 35 and/or source voltages 33 may provide for the method described herein a means to adapt to and be effective in detecting a deterioration in suspension members with varied characteristics, for example, suspension length and/or the number of cords per suspension member, or to any type of suspension with conductive cords.

2.) The net sum current flow of the multi-phase circuit is most easily obtained by measuring a change in an unbalanced load current between the common point of the supply-side and the load side of the multi-phase circuit, commonly called the neutral wire, for example in a Wye-configured arrangement, but can of course be obtained by measuring the current through each phase (phase current) and summing them together. Although a three phase WYE-configuration may be a preferred embodiment, any multi-phase configuration can be used where peak current in each phase is shifted by a phase angle between them.

As advantages, for example multi-phase circuits allow for a least number of connections to power the steel cords and all suspension members in an elevator, and to monitor the net sum phase current. As few as two connections to the cords are required to power the cords and none are required to be connected to the cords when a current transformer is used to monitor the net sum of the phase currents. The loss of continuity of current flow in any phase will cause a change in the net sum phase current.

3.) Different methods and devices can be used for transformation of the net sum of the multi-phase current flow into a signal that is proportional to, or triggers that there is a change in the cross sectional area and strength of the steel cords comprised in the multi-phase circuits. For example, there are various types of current transformers that can be designed and arranged to provide secondary voltage and current that is proportional to the primary current developed in the multi-phase circuits comprising the steel cord conductors being monitored.

Examples of current transformers include the Rogowski transformer and the step up, step down, or one to one isolation transformer, where in the net sum of the current flow of the steel conductors flows in the primary of the transformer and the secondary of the transformer produces a current proportional to the primary current and is supervised as a signal for the purpose of monitoring of the physical condition of the steel cords.

Another embodiment for measuring the net sum of the current flow is to use a Hall effect generator (sensor) in combination with a magnetic core that surrounds the neutral wire and an amplifier that provides a proportional output voltage signal.

There may be other embodiments for measuring the net sum of the phase currents that are known, or can be developed by those skilled in the art who read this invention.

As possible advantages, no physical connection to the steel cords is required by the monitoring device. Furthermore, electrical isolation may be provided, application of CTs is ideal in "noisy" environments and is low cost and highly reliable. Furthermore, advantage may be taken of transformer behavior, such as magnetic saturation, to create signals in low complexity monitoring circuits. Furthermore, flexibility for arranging the circuits in primary and secondary of the transformer may be obtained.

4.) The steel cords of the suspension members can be arranged to create "conductors" that carry power in parallel, series, or a combination of the two in the multi-phase circuits.

As possible advantages, ability to optimize the physical arrangement of electrical connections to conductor cords for suspension members with varied characteristics, for example, suspension length and/or the number of cords per suspension member, or to any type of suspension with conductive cords, while minimizing the number of unique electrical connections: 1) between cord conductors, 2) between cord conductors and multi-phase power, 3) between cord conductors and a common neutral point when used, and between cords of all suspension members.

As further possible advantages, the monitoring of the net sum of phase current in all the cord conductors can be resolved as proportional to the physical properties of the cords (change in cross sectional area). The cords act only as power circuit conductors in the multi-phase circuits when a CT is used for monitoring the net sum of the phase currents.

Furthermore, specifically in embodiments where all phases of the multi-phase alternating current are fed through at least one of the cords of the suspension members, there may be no need or at least a relaxed need for any temperature compensation since equal changes in temperature in each of the cords generally result in equal changes in electro-physical characteristics of these cords such that all current phases are affected in similar ways and the net sum current or bypass current through the neutral wire, i.e. the indicator current, remains unaffected by such temperature changes.

Finally, it should be noted that terms such as "comprising" do not exclude other elements or steps and that terms such as "a" or "an" do not exclude a plurality. Also elements described in association with different embodiments may be combined.

LIST OF REFERENCE SIGNS 1 elevator
3 car
5 counterweight
7 elevator shaft
9 suspension member arrangement
11 suspension member
13 fraction machine
15 traction sheave
17 device for detecting deterioration
19 belt
21 matrix material
23 cords
25 electrical component
27 leg
29 common point
31 multi-phase alternating current circuitry
33 source side
35 load side
37 neutral wire
39 measuring device
41 current transformer
43 secondary winding arrangement
45 analyzing arrangement
47 bridge member
49 resistive load
a, b, c lines of legs
Va, Vb, Vc alternating voltages
$I_a$, $I_b$, $I_c$ alternating currents
Zya, Zyb, Zyc resistances in legs
$I_n$ bypass current
Zn resistance in neutral wire

What is claimed is:

1. A method for detecting a deterioration state of a load bearing capacity in a suspension member arrangement for an elevator, the suspension member arrangement including a suspension member having a plurality of electrically conductive cords, the method comprising the steps of
    providing a multi-phase alternating current circuitry including multiple electrically conductive legs;
    applying at least one phase of a multi-phase alternating current to at least one of the cords of the suspension member being electrically connected to one of the legs of the multi-phase alternating current circuitry;
    applying at least one other phase of the multi-phase alternating current to at least one of another one of the cords of the suspension member and at least one separate resistor being electrically connected to at least one other leg of the multi-phase alternating current circuitry, wherein a peak current in each phase is shifted by a phase angle with respect to a peak current in another phase;
    measuring an electric indicator current being at least one of a net sum of all phases of the multi-phase alternating current and an electric bypass current through a neutral wire being connected in parallel to the multi-phase alternating current circuitry; and
    determining the deterioration state of the suspension member arrangement based on the measured electric indicator current.

2. The method according to claim 1 wherein the deterioration state is determined based on a deviation of the measured electric indicator current from a reference current value.

3. The method according to claim 2 wherein a critical deterioration state is detected based upon the measured electric indicator current deviating from the reference current value by more than a predetermined difference value.

4. The method according to claim 1 wherein the electric indicator current is measured using a measuring arrangement including a measuring device for contactless measuring of an electrical current in a conductor.

5. The method according to claim 1 wherein the electric indicator current is measured using a measuring device being one of a current transformer and a Hall effect current sensor.

6. The method according to claim 5 wherein the measuring device is arranged at one of the multi-phase alternating current circuitry and the neutral wire.

7. The method according to claim 1 wherein the multi-phase alternating current circuitry is in a Wye-configuration.

8. The method according to claim 1 wherein the neutral wire is connected between common points of a supply side of the multi-phase alternating current circuitry and a load side of the multi-phase alternating current circuitry, respectively.

9. The method according to claim 1 wherein each of the phases of the multi-phase alternating current is applied to at least one of the cords of the suspension member.

10. The method according to claim 1 wherein, in an initial state before deterioration, electrical resistances within each of the legs of the multi-phase alternating current circuitry are adapted to be substantially equal.

11. The method according to claim 1 wherein several of the cords of the suspension member are connected together in at least one of a parallel arrangement and a series arrangement.

12. The method according to claim 1 wherein the suspension member arrangement includes a plurality of the suspension member and wherein cords of one of the suspension members are connected in at least one of a parallel arrangement and a series arrangement to cords of another one of the suspension members.

13. The method according to claim 1 wherein the phases of the multi-phase alternating current are supplied with an even phase offset from each other.

14. A device for detecting a deterioration state of a load bearing capacity in a suspension member arrangement for an elevator, the suspension member arrangement including a suspension member having a plurality of electrically conductive cords, comprising:
a multi-phase alternating current circuitry having multiple legs, each of the legs including an AC voltage supply to apply each of multiple phases of a multi-phase alternating current to one of the legs;
a connector arrangement for electrically connecting the multi-phase alternating current circuitry to the suspension member such that at least one phase of the multi-phase alternating current is applied to at least one of the cords of the suspension member and such that at least one other phase of the multi-phase alternating current is applied to at least one of another one of the cords and at least one separate resistor;
a measuring arrangement configured for measuring an electric indicator current being at least one of a net sum of all phases of the multi-phase alternating current and an electric bypass current through a neutral wire connected in parallel to the multi-phase alternating current circuitry; and
an analyzing arrangement for determining the deterioration state based on the measured electric indicator current.

15. The device according to claim 14 wherein the measuring arrangement includes a measuring device for contactless measuring of an electrical current in a conductor.

16. An elevator including the device according to claim 14 and the suspension member arrangement.

17. A method for detecting a deterioration state of a load bearing capacity in a suspension member arrangement for an elevator, the suspension member arrangement comprising at least one suspension member having a plurality of electrically conductive cords, the method comprising:
providing a multi-phase alternating current circuitry including multiple electrically conductive legs;
applying at least one phase of a multi-phase alternating current to at least one of the cords of the suspension member by being electrically connected to one of the legs of the multi-phase alternating current circuitry;
applying at least one other phase of the multi-phase alternating current to at least one of another at least one cord of the suspension member and at least one separate resistor being electrically connected to at least one other leg of the multi-phase alternating current circuitry, wherein a peak current in each phase is shifted by a phase angle with respect to a peak current in another phase;
measuring an electric indicator current being at least one of a net sum of all phases of the multi-phase alternating current and an electric bypass current through a neutral wire being connected in parallel to the multi-phase alternating current circuitry; and
determining the deterioration state based on the measured electric indicator current.

18. A device for detecting a deterioration state of a load bearing capacity in a suspension member arrangement for an elevator, the suspension member arrangement including at least one suspension member having a plurality of electrically conductive cords, wherein the device is configured to perform the method according to claim 17, the device comprising: the multi-phase alternating current circuitry, a measuring device for measuring the electric indicator current and an analyzing arrangement for determining the deterioration state.

* * * * *